(12) United States Patent
Hirszowicz et al.

(10) Patent No.: US 7,040,892 B2
(45) Date of Patent: May 9, 2006

(54) LASER INSTRUMENT FOR ENDODONTIC TREATMENT

(75) Inventors: Eran Hirszowicz, Ramat Gan (IL); Yemini Rannan, Kfar Vitkin (IL); Ytzhak Rozenberg, Ramat Gan (IL); Adam Stabholz, Jerusalem (IL)

(73) Assignee: Opusdent Ltd., Yokneam (IL)

( * ) Notice: Subject to any disclaimer, the term of this patent is extended or adjusted under 35 U.S.C. 154(b) by 0 days.

(21) Appl. No.: 10/386,117

(22) Filed: Mar. 12, 2003

(65) Prior Publication Data

US 2004/0038170 A1      Feb. 26, 2004

(30) Foreign Application Priority Data

Mar. 12, 2002   (IL) ..................................... 148653

(51) Int. Cl.
*A61C 1/00*      (2006.01)

(52) U.S. Cl. ............................ 433/29; 433/215; 606/15
(58) Field of Classification Search ................ 433/29, 433/215; 606/15, 16, 17; 607/89, 93; 385/903
See application file for complete search history.

(56) References Cited

U.S. PATENT DOCUMENTS

| 5,496,308 | A | * | 3/1996 | Brown et al. | .................. 606/15 |
| 6,113,589 | A | * | 9/2000 | Levy et al. | .................. 606/16 |

\* cited by examiner

*Primary Examiner*—Cary E. O'Connor
(74) *Attorney, Agent, or Firm*—Pearl Cohen Zedek Latzer, LLP

(57) ABSTRACT

An apparatus and a system including a side firing laser head to be used in a wide variety of medical, dental and other procedures, the side firing laser head having an elongated spiral slit extending along the laser head, but not extending to the tip portion of the laser head.

25 Claims, 8 Drawing Sheets

LASER INSTRUMENT FOR ENDODONTIC TREATMENT

FIELD OF THE INVENTION

The present invention relates generally to the field of surgical laser-heads and/or laser tips, more specifically, the present invention relates to a laser-head for example especially useful for utilizing laser radiation in root canal procedures.

BACKGROUND OF THE INVENTION

Laser radiation treatments have become common practice in many medical procedures. However, various technical obstacles prevent an even more extensive and efficient use of laser technology in many additional medical and dental procedures.

A successful endodontic procedure may preferably provide a patient with a long lasting reliable solution. Current endodontic procedures require that any organic or inorganic debris such as inflamed or necrotic tissue, microorganisms and/or dentinal remnants are completely removed from the root canal cavity before the filling material is applied into the root canal cavity. Traditional methods of cleaning and sterilizing the root canal cavity are unsatisfactory.

Another challenge of a successful endodontic procedure is preventing foreign bodies such as microorganisms from entering the treated root canal through microscopic tubes known as dentinal tubules. The dentinal tubules extend from the root canal walls to a thin protective layer known as the cementum layer. The cementum layer separates the dentinal tubules from the soft tissue surrounding the tooth. Unfortunately, the cementum layer may be eroded or damaged over the years leaving the openings of the dentinal tubules exposed and accessible to foreign bodies. Invasion of foreign bodies into the root canal is therefore a long run threat to health of a treated tooth's. Current solutions aimed at reducing the risk of foreign bodies invasion into the treated root canal are also unsatisfactory.

Attempts have been made to replace the traditional endodontic treatment methods with methods utilizing laser radiation. Although laser radiation is believed be potentially more suitable for endodontic procedures, various complication have thus far prevented endodontic treatment methods utilizing laser radiation from becoming widely accepted. While laser radiation may enable a more through cleaning of organic and/or inorganic debris and sterilizing, it was discovered that the laser radiation may also be absorbed by the delicate nerves located beyond the root end opening, thereby causing pain and even permanent damage to the patient. It has been suggested to use side firing laser heads in order to prevent the laser radiation from being emitted along the vertical axis of the laser head and thus minimize the exposure of the nerves to the laser radiation. However, current side firing laser heads are inflexible and brittle and are therefore unsuitable for use in endodontic procedures.

SUMMARY OF THE INVENTION

According to an embodiment of the present invention a side firing laser head having an elongated spiral slit extending along the laser head, but not extending to the tip portion of the laser head may be used in a wide variety of medical, dental and other procedures.

Figure 1A:
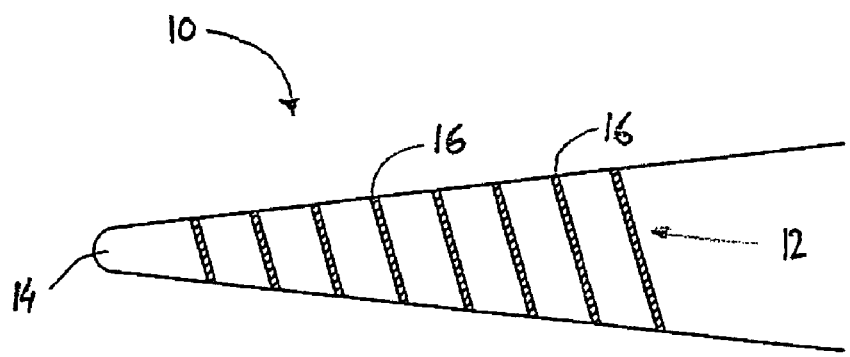
FIG. 1A is a diagram illustrating the basic mode of a laser head according to an embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

FIG. 1A illustrates a side firing laser head 10 according to an embodiment of the present invention. The laser head 10 may have an elongated spiral slit 12 extending along a portion of the laser head 10, but typically not extending to the tip portion 14 of the laser head 10.

In accordance with an embodiment of the present invention the spiral slit 12 along a portion of the laser head 10 permits lateral emission of the laser radiation. Typically the spiral slit 12 does not extend however to the tip portion 14 of the laser head 10, such that no electromagnetic radiation may be emitted from the tip portion 14 of the laser head 10. The design of the laser head 10 of the present invention prevents the irradiation of laser radiation out of the laser head 10 through the canal end opening and onto the delicate nerves located thereabout, while allowing a substantially perpendicular of laser radiation through the elongated spiral slit 12 onto the walls of the root canal, such that the laser radiation may be directed onto the wall of the root canal without the risk of the laser radiation affecting the nerves.

Figure 1B:
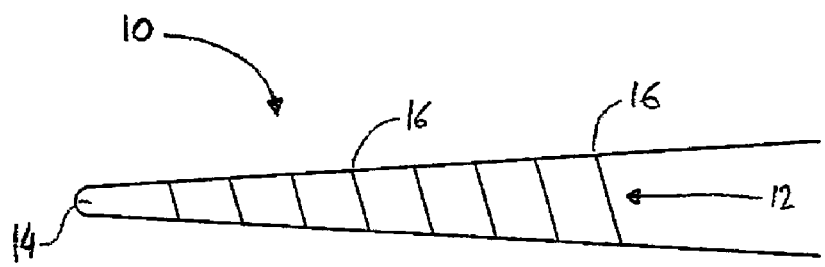
FIG. 1B is a diagram illustrating the narrow mode of a laser head according to an embodiment of the present invention.

FIG. 1B illustrates the narrow mode of the laser head 10 according to an embodiment of the present invention. The elongated slit 12 design of the laser head of the present invention may enable the adjustment of the diameter of the laser head 10 or the adjustment of the diameter of a portion of the laser head 10. For example, the application of torque force onto the laser head 10 may cause the laser head 10 to twist and curl and by partially closing the gaps 16 of the elongated slit 12 thereby reducing the diameter of the laser head 10 or the diameter of a portion of the laser head 10. It should be emphasized that in the narrow mode of the laser head 10 according to an embodiment of the present invention, wherein the gaps 16 of the elongated slit 12 along a portion of the laser head 10 are partially closed the functionality of the laser head 10 is maintained and the laser radiation is allowed to exit the laser head 10 through the elongated slit 12.

Figure 1C:
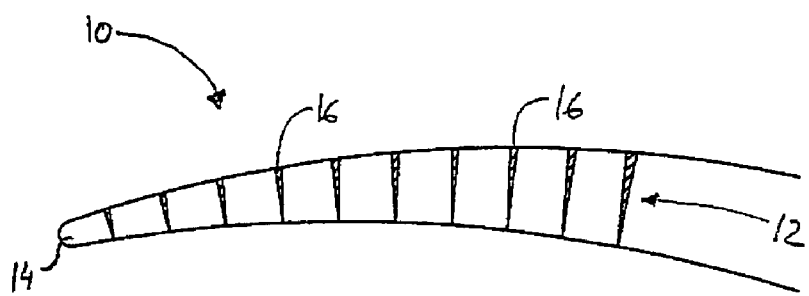
FIG. 1C is a diagram illustrating the curved mode of a laser head according to an embodiment of the present invention.

Turning now to FIG. 1C there is shown a laser head 10 according to an embodiment of the present invention in a curved mode. The elongated slit design of the laser head 10 of the present embodiment may allow the laser head 10 to curve and flex without breaking. The flexibility of the laser head 10 according to the present embodiment may enable the laser head 10 to adjust itself in accordance with the contour of a cavity into which the laser head 10 may be advance, thus enhancing the accessibility of the laser head 10. According to an embodiment of the present invention the laser head 10 may be pre-adjusted to improve the accessibility of the laser head 10 and/or in order to confirm with the treatment requirements.

Figure 2:
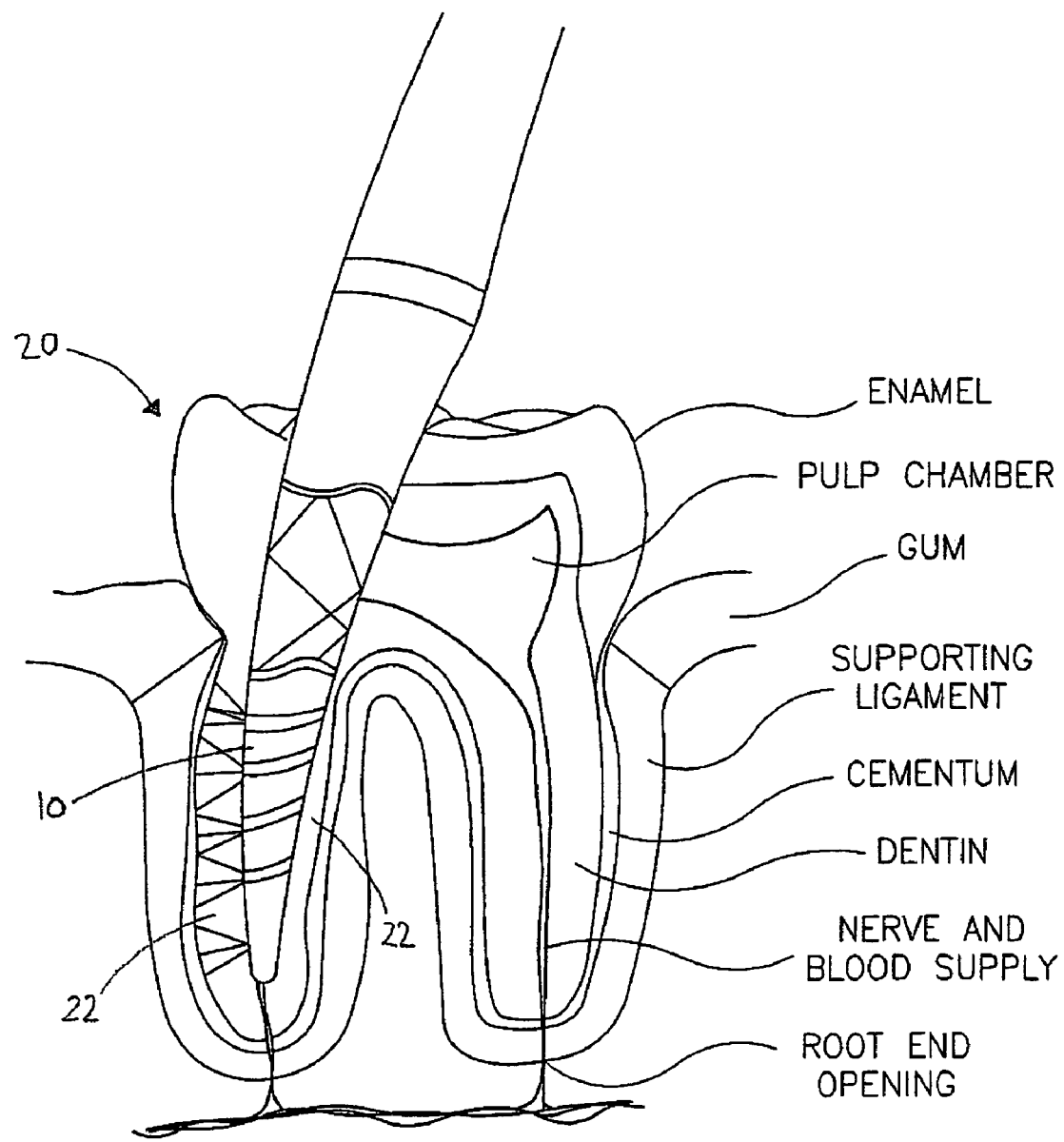
FIG. 2 is a schematic illustration of an embodiment of the laser headpiece of the present invention inside a patient's tooth.

Turning now to FIG. 2 there is shown a laser head 10 according to an embodiment of the present invention inside a patient's tooth. FIG. 2 illustrates some of the advantages of the laser head 10 of the present invention when utilized for performing root canal treatment although it should be noted that other uses are possible. Typically the physical structure of a root canal is substantially narrow, curved and tapered. The advantages of the laser head 10 of the present invention may be illustrated by its suitability for performing laser treatments in narrow, curved spaces such as the root canal of a patient's tooth 20.

The laser head 10 of the present invention may be used in conjunction with one or more traditional endodontic treatment techniques and/or treatment tools. For example, the operator may use a mechanical drill to drill a hole into the cap of the patient's tooth 20, exposing the root canal cavity. The operator may then choose to use a mechanical reamer in order to remove the pulp tissue from the root canal. As discussed above a mechanical reamer provides only limited results when used for cleaning and sterilizing the cavity of the root canal and may also be replaced with a laser head according to the present invention. Either as a supplement or as a replacement altogether the operator may utilize the laser head 10 of the present invention to irradiate the walls 22 of the root canal with laser radiation having a first wavelength or wavelengths, thereby evaporating substantially all the organic and/or inorganic debris in the root canal cavity and/or in the dentinal tubules. After the root canal cavity and the dentinal tubules have been cleaned and sterilized the operator may utilize the laser head 10 to irradiate the walls 22 of the root canal with sufficient laser radiation having a first wavelength or wavelengths or a second wavelength or wavelengths to cause the root canal walls 22 to melt thus sealing the dentinal tubules.

The process described above may be achieved, for example, by advancing the laser head 10 according to some embodiments of the present invention into the root canal cavity of a patient's tooth 20 and activating a laser source that may be operatively connected to the laser head 10 as discussed in greater detail hereinbelow to cause laser radiation generated by the laser source to be irradiated out of the laser head 10 through the elongated slit 12 onto the walls 22 of the root canal. The laser radiation may evaporate and/or destroy organic and/or inorganic debris in the root canal and/or in the dentinal tubules. In addition or in alternative the laser radiation may cause the root canal walls 22 to melt thereby closing the dentinal tubules. According to some embodiments of the present invention the laser head 10 may be advanced through the root canal substantially to the apical end of the root canal such that the laser radiation from the laser head 10 may clean and/or sterilize the entire cavity of the root canal and/or the dentinal tubules and/or melt the root canal walls 22 throughout such that the root canal cavity may possibly be hermetically sealed. As discussed above the elongated slit 12 design of the laser head 10 according to an embodiment of the present invention may allow the laser head 10 to bend and curve and/or to be adjusted, for example, according to the size constraints dictated by the root canal's anatomy. The adjustability and flexibility of the laser head 10 according to some embodiments of the present invention may improve the accessibility of the laser head 10 and possibly allowing the operator to advance the laser head 10 substantially to the apical end of the root canal without the risk of breaking the laser head 10 inside the patient's tooth 20, while insuring that the root canal walls 22 are irradiated with laser radiation throughout.

Once the dentinal walls 22 have been melted a filling material may be inserted into the root canal cavity and condensed such that the root canal cavity is completely and hermetically filled.

Figure 3:
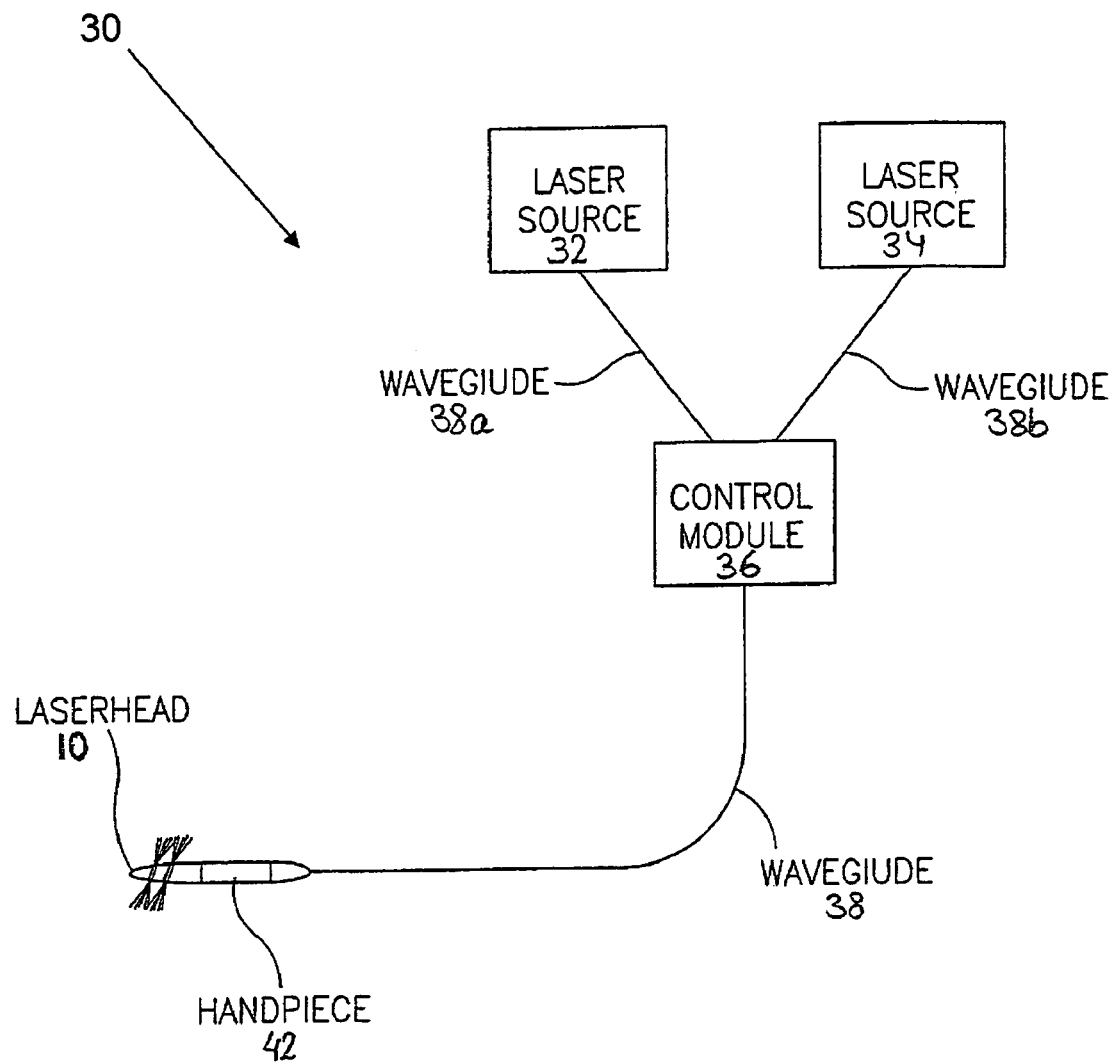
FIG. 3 is a block diagram showing a laser system according an embodiment of the present invention.

Turning now to FIG. 3 there is shown a laser system 30 according to an embodiment of the present invention. The laser system 30 comprising a first laser source 32 and a second laser source 34. The first laser source 32 may be adapted to produce laser radiation having a first wavelength and the second laser source 34 may be adapted to produce laser radiation having a second wavelength. The first and the second laser sources 32, 34 may be connected to a control module 36. The first laser source 32 and the second laser source 34 may be connected to a guidance element 38, for example a waveguide. The first laser source 32 may be connected to a first guidance element 38a and the second laser source 34 may be connected to a second guidance element 38b. The first and the second laser sources 32, 34 may also be conjointly connected to a single guidance element 38, for example using optical elements such as lenses to focus the electromagnetic radiation from both first and second laser sources 32, 34 into the single guidance element 38. The guidance element 38 may be connected to a handpiece 42. The handpiece 42 maybe operatively connected to the laser head 10 according to an embodiment of the present invention. The laser system 30 of the present invention may further comprise a control element 36 or some other control equipment. The control element 36 may be adapted for example to control the output of the first laser source 32 or the second laser source 34 and/or to control the output of the laser head 10.

According to one embodiment of the present invention the control module 36 may be coupled to the handpiece 42.

According to another embodiment of the present invention the control module 36 may be coupled to the laser source or sources 32, 34.

According to an embodiment of the present invention the control module 36 may include a Q-switch (not shown). The Q-switch may be adapted to control the output of the control switch (not shown).

According to another embodiment of the present invention the control module 36 may include a mechanical shutter (not shown). The mechanical shutter may be adapted to control the output of the laser head 10.

According to an embodiment of the present invention the control module 36 may be adapted to control the operation of the first laser source 32 and the second laser source 34. For example, the control module 36 may be adapted to control the operation of the first laser source 32 and the second laser source 34 such that the laser head 10 may irradiate laser radiation having a first wavelength, a second wavelength or a combination of the laser radiation having a first wavelength and the laser radiation having a second wavelength. It will be obvious to those with ordinary skill in the art that a flexible control protocol in accordance with some embodiments of the laser system 30 of the present invention may be preferable for use in a wide range of tasks procedures. It is emphasized that the laser system 30 in accordance with some embodiments of the present invention may comprise other equipment or controls having various configurations.

Figure 4:
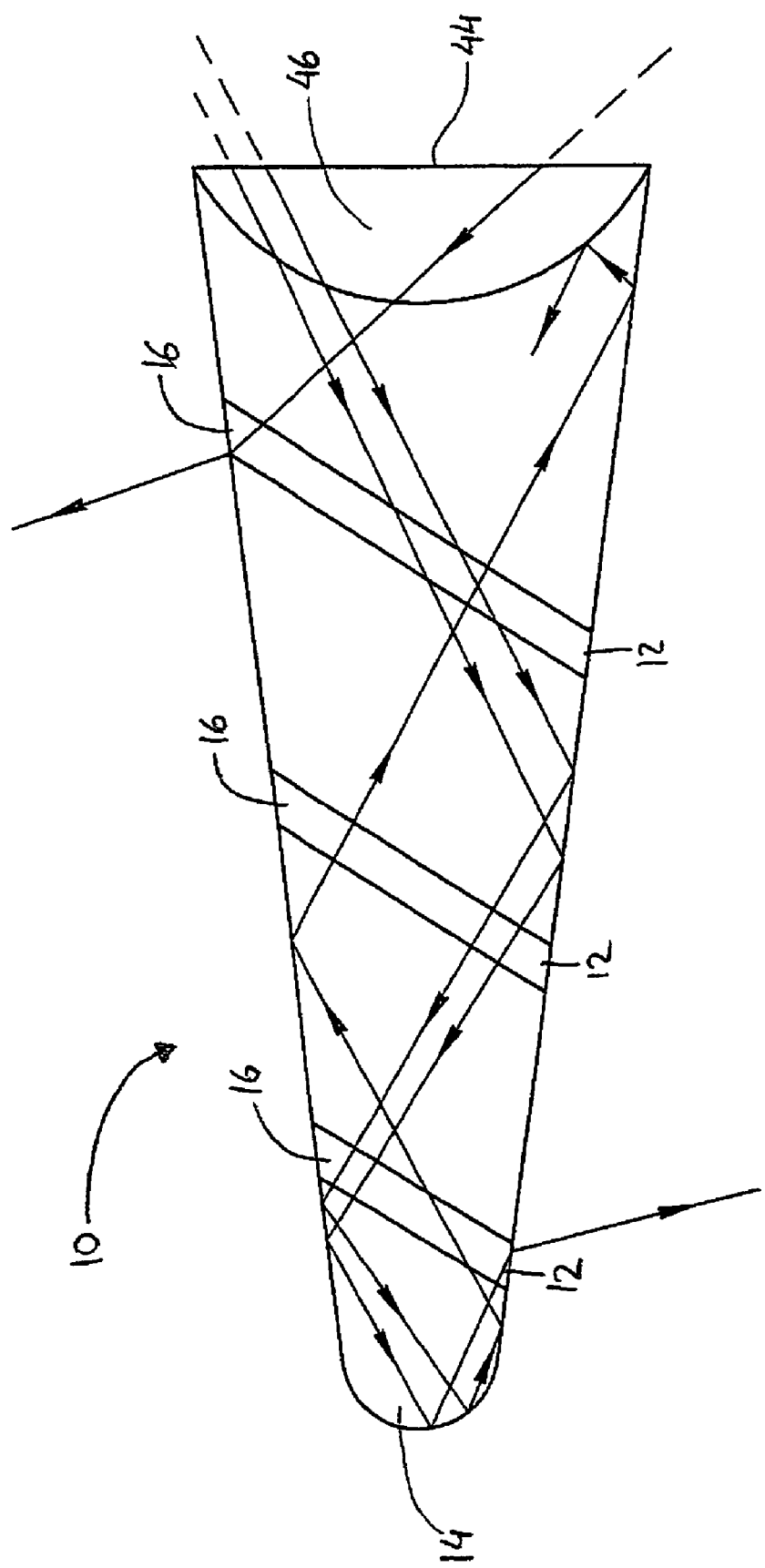
FIG. 4 is a cross sectional illustration of an embodiment of the laser head of the present invention.

Turning now to FIG. 4 there is shown a cross section of a laser head 10 according to an embodiment of the present invention. Incoming laser radiation may enter the laser head 10 and may propagate through the laser head 10 in a series of internal reflections as detailed in greater detail herein below. The incoming laser radiation may propagate in a general direction from the entrance portion 44 of the laser head 10 to the tip portion 14 of the laser head 10. A portion of the incoming laser radiation may escape the laser head 10 through the elongated slit 12 along a portion of the laser head 10 according to some embodiments of the present invention and may be emitted out of the laser head 10. The laser radiation may be emitted substantially perpendicularly to the propagation axis of the incoming laser radiation. Possibly a portion of the incoming laser radiation may fail to escape the laser head 10 through the elongated slit 12 and may thus continue to propagate and may reach the tip portion 14 of the laser head 10. The tip portion 14 of the laser head 10 may be blocked according to some embodiments of the present invention such that the incoming laser radiation may be reflected by the tip portion 14 of the laser head 10 such that the direction of the propagation of the reflected laser may be substantially opposite to the direction of the propagation of the incoming laser radiation. The reflected laser radiation may propagate through the laser head 10 in a series of internal reflections. A portion of the reflected laser radiation may escape the laser head 10 through the elongated slit 12 along a portion of the laser head 10 according to some embodiments of the present invention and may be emitted out of the laser head 10. The reflected laser radiation may be emitted substantially perpendicularly to the propagation axis of the reflected laser radiation. Possibly a portion of the reflected laser radiation may fail to escape the laser head 10 through the elongated slit 12 and may thus continue to propagate and may reach the entrance portion 44 of the laser head 10. According to an embodiment of the present invention the entrance portion 44 of the laser head 10 may comprise an optical element 46, for example a bipolar lens. The optical element 46 may be adapted to allow the incoming radiation to enter the laser head 10 and to reflect the reflected laser radiation such that the reflected laser radiation may not escape the laser head 10 through the entrance portion 44 of the laser head 10.

Figure 5A:
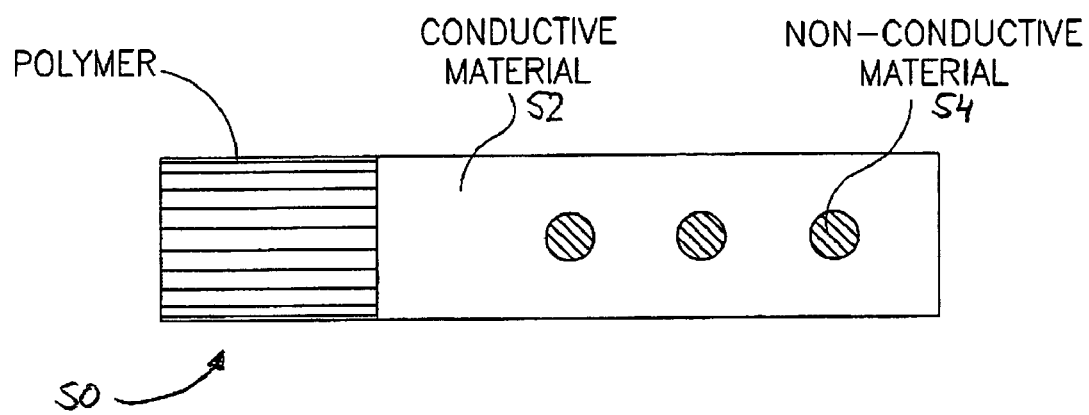
FIG. 5A is a block diagram illustration of a first mold used in the manufacturing process of a laser head according to one embodiment of the present invention.
Figure 5B:
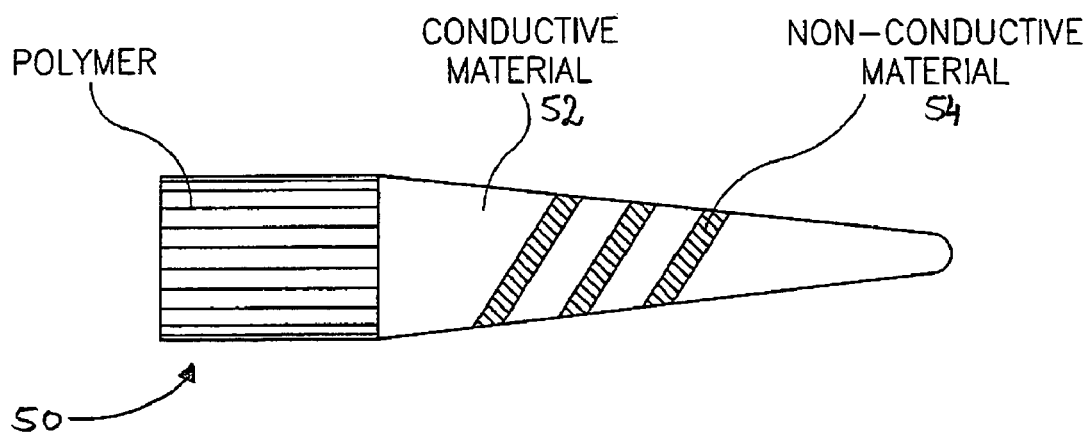
FIG. 5B is a block diagram illustration of a second mold used in the manufacturing process of a laser head according to another embodiment of the present invention.

Referring to FIGS. 5A and 5B, a mold 50 structure is created from, for example, a polymer material; other suitable non-conductive material may be used to form the mold 50. While a certain set of shapes, with a certain set of surface patterns, is shown in the FIGS., other suitable shapes and forms and surface patterns may be used. The mold 50 may be coated in certain places with conductive material 52 (e.g., metal such as stainless steel or other suitable substances), through suitable methods such as plating or painting. A conductive and a non-conductive pattern is created on the surface. Alternately, a polymer structure or a portion of a polymer structure may be substantially coated with a conductive material 52 with a non conductive material 54 applied over this coating in a pattern. Painting may be, for example, automatic, through spray or air painting methods, by hand, and/or through other methods. Views of such a mold 50 may be seen in FIGS. 5A and 5B One method of applying conductive material 52 may be to coat portions a polymer object with non-conductive material 54 and plate this structure; the plating material will attach to the polymer.

Figure 6A:
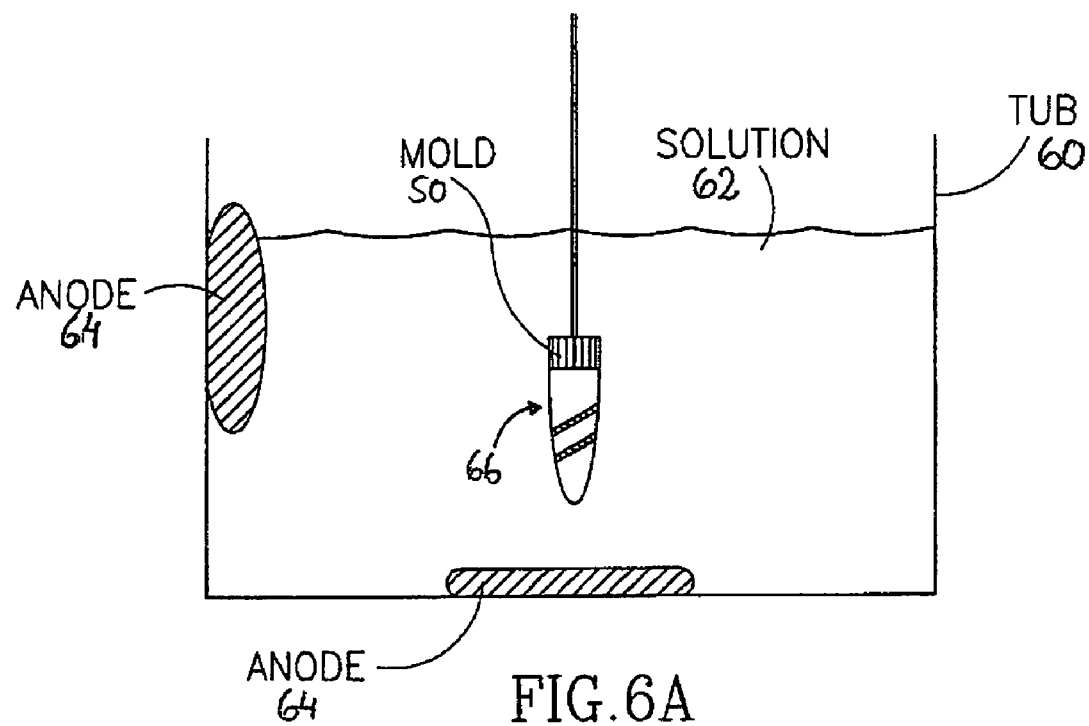
FIG. 6A is a block diagram illustration of an electroplating process for producing the laser head according to an embodiment of the present invention.

Turning now to FIG. 6A there is shown an electroplating process according an embodiment of the present invention. The mold 50 may be dipped or placed in an electroplating tub 60. Ionized iodine may be used as the electrolytic solution 62, a silver electrode may be used as the anode 64 and the conductive material 52 deposited onto the mold 50 may be used as the cathode 66. According to an embodiment of the present invention the plating layer may possibly form only on portions of the mold 50 that have been pre-plated with a conductive material 52 which is exposed and not covered if a non-conductive coating is used. It may thus be possible to design a laser head shell that will copy the design of the mold 50 and the pattern of the conductive layer 52 deposited thereon.

According to an embodiment of the present invention the duration of the plating process may be selected in accordance with the desirable thickness of the plating layer.

Figure 6B:
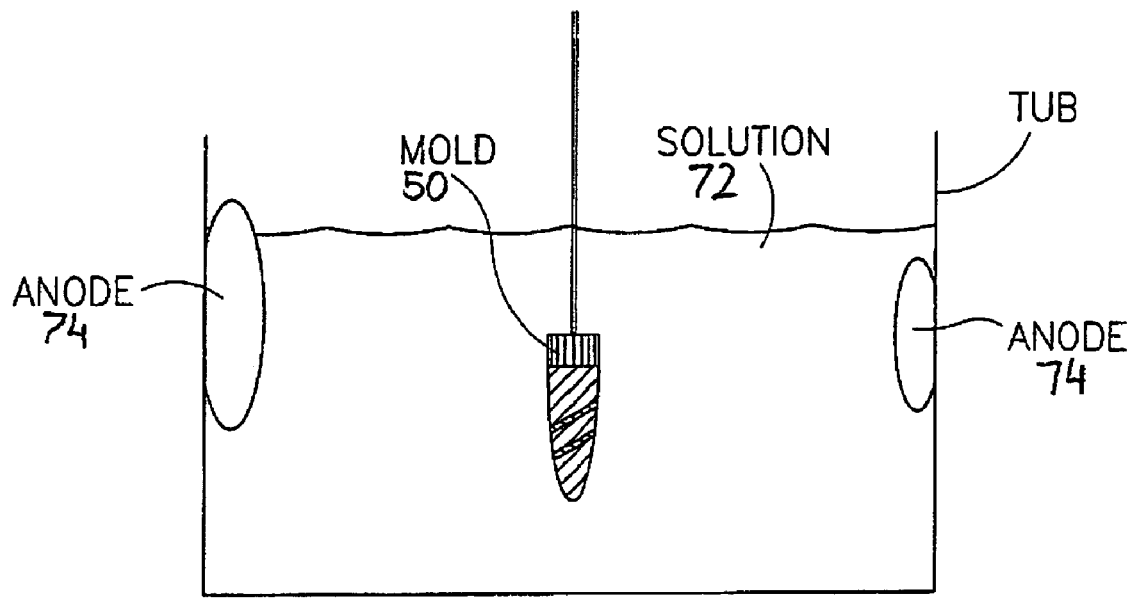
FIG. 6B is a block diagram illustration of an electroplating process for producing the laser head according to an embodiment of the present invention.

Turning now to FIG. 6B there is shown a layering process according to an embodiment of the present invention. The first electroplating process discussed above may be repeated with a second electrolytic solution 72, for example ionized gold and/or a second anode 74, for example a gold electrode such that a second layer may be deposited on the first layer discussed above.

Other layering methods may also be used either in conjunction with the method discussed above or instead of the layering methods discussed above.

Figure 7:
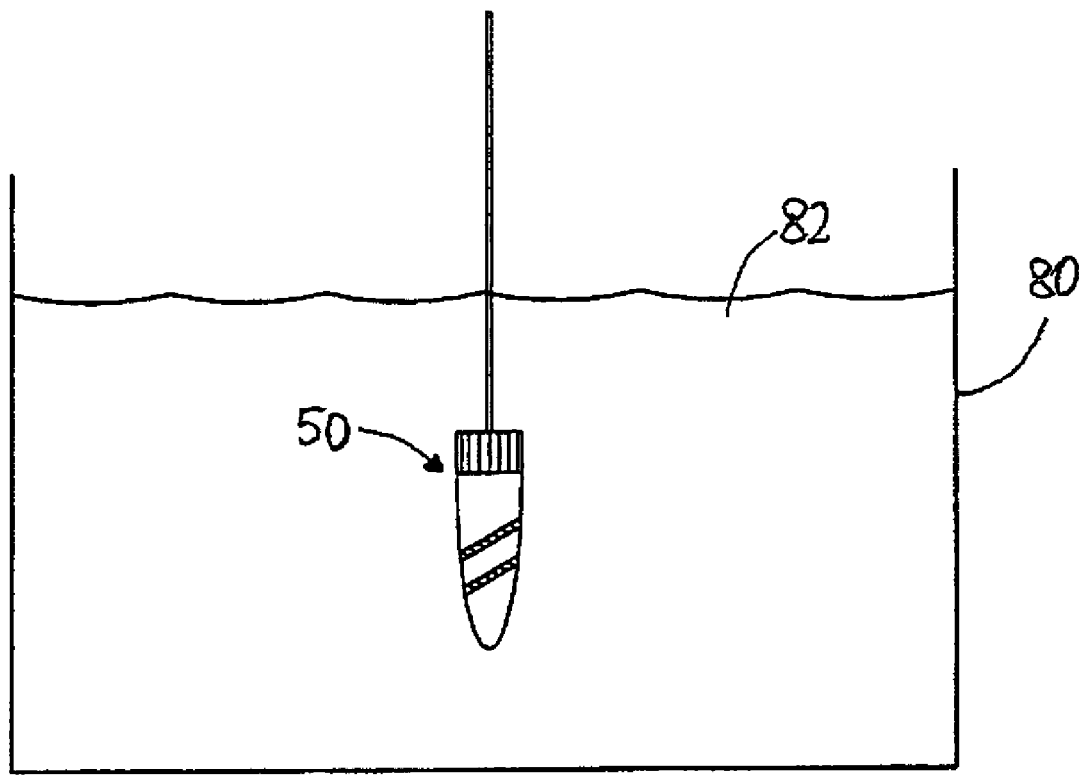
FIG. 7 is a block diagram illustration of an extraction process of the laser head according to an embodiment of the present invention.

Turning now to FIG. 7 there is shown the extraction process of the mold 50 according to an embodiment of the present invention. Once the plating has been completed, the mold 50 may be extracted out of the laser head 10. After the mold 50 has been extracted The laser head 10 may retain the shape and the contour of the mold 50 and the patterns of the exposed conductive material 52. According to an embodiment of the present invention the mold 50 may be dipped in a glass container 80 containing an acid 82. The acid 82 may cause the mold 50 to melt while not affecting the layer(s). Other methods of removing the mold 50 may be used.

The laser head 10 may be cleaned and polished for example by using a chemical polish in order to smoothen the inner surface of the laser head 10. A smooth inner surface may improve the radiation conductivity of the laser head 10.

According to one embodiment of the present invention the inner surface of the laser head 10 may be layered with a dielectric layer or any other suitable substance, such as a silver iodine silver bromide, gold or any other metal, for improving the conductivity of the laser head 10. A gas or a liquid solution may be pumped through the laser head 10 and may react with the inner layer of the laser head 10 such that a new, dielectric inner layer may be formed. When the laser head 10 is exposed to moisture it may be preferable to use a non-dielectric substance in order to maintain a relatively high level of conductivity.

The above discussion of a side firing laser head 10 in accordance with some embodiments of the present invention for endodontic purposes is a mere illustration of one field in which it may be beneficial to use a laser head 10 according to some embodiments of the present invention, however numerous other medical, dental and non-medical procedures may also benefit from using a laser head 10 in accordance with some embodiments of the present invention.

Figure 8A:
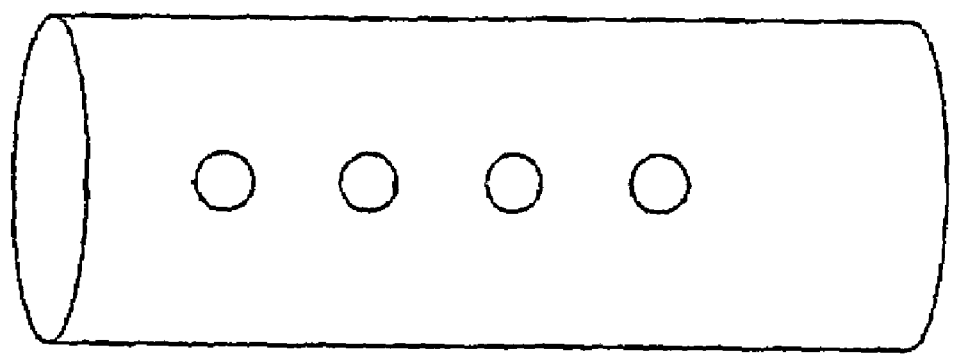
FIG. 8A is a block diagram illustration of a first laser head according to one embodiment of the present invention.
Figure 8B:
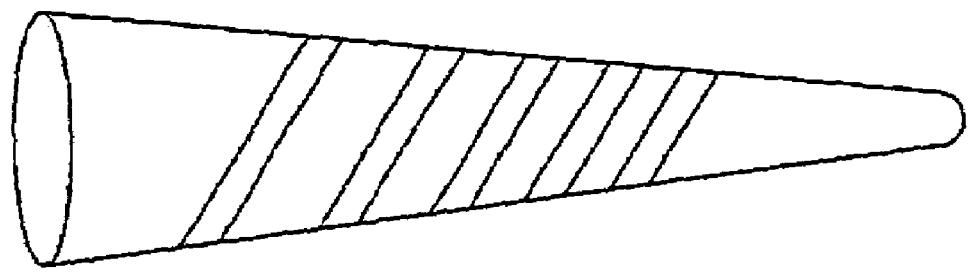
FIG. 8B is a block diagram illustration of a second laser head according to another embodiment of the present invention.

FIGS. 8A and 8B illustrate additional embodiments of the present invention.

It will be appreciated by persons skilled in the art that the present invention is not limited by what has been particularly shown and described hereinabove. Rather the scope of the invention is defined by the claims that follow:

What we claim is:

1. A dental treatment apparatus including a side firing laser head having an elongated spiral slit extending along the laser head, but not extending to the tip portion of the laser head, wherein gaps in said spiral slit are capable of being adjusted by application of a force to the apparatus.

2. The dental treatment tool of claim 1, wherein said side firing laser head is configured to permit lateral emission of a laser radiation.

3. The dental treatment tool of claim 2, wherein said side firing laser head is further configured to prevent said laser radiation from being emitted longitudinally.

4. The dental treatment tool of claim 3, wherein said side firing laser head is configured to permit said laser radiation to affect at least a portion of the side walls of the root canal.

5. The dental treatment tool of claim 4, wherein said side firing laser head is configured to prevent a substantial effect of the laser radiation on the nerves located beyond the apical tip of the root canal.

6. The dental treatment tool of claim 5, wherein said laser head, when positioned within a patient's root canal may be operated to sterilize an inner cavity of the patient's root canal.

7. The dental treatment tool of claim 6, wherein said laser head, when positioned within a patient's root canal may be operated to melt the inner dentinal walls of the root canal, such that the tubules are substantially sealed.

8. The dental treatment tool of claim 1, wherein said gaps are capable of being adjusted by varying the diameter of at least a portion of the laser head.

9. The dental treatment tool of claim 8, wherein diameter of at least a portion of the laser head may be adjusted by twisting at least a portion of the laser head.

10. The dental treatment tool of claim 1, wherein said elongated slit is configured to render at least a portion of the laser head flexible.

11. The dental treatment tool of claim 10, wherein at least a portion of said laser head is configured to curl in response to a torque force applied onto that portion.

12. The dental treatment tool of claim 11, wherein said at least portion of said laser head is configured to return to its original form when the application of torque force is discontinued.

13. The dental treatment tool of claim 11, wherein said spiral slit enables said laser head to access a patient's root canal.

14. The dental treatment tool of claim 11, wherein said spiral slit enables said laser head to access substantially the full length of a patient's root canal, such that the tip of said laser head is located at substantially the apical end of the root canal.

15. The dental treatment tool of claim 11, wherein said spiral slit enables said laser head to access the full length of a plurality of a patient's root canals having different contours and diameters, such that the tip of said laser head is located at substantially the apical end of the root canal.

16. The dental treatment tool of claim 1, wherein said elongated spiral split is comprised of a plurality of substantially contiguous slits, and wherein said plurality of substantially contiguous slits are configured to function in a manner substantially identical to a continuous elongated spiral slit at least in terms of laser irradiation, flexibility and adjustability.

17. A method of treating a patient's tooth comprising:
    positioning inside a root canal of the patient's tooth a side firing laser head having an elongated spiral slit extending along the laser head, but not extending to the tip portion of the laser head;
    adjusting gaps in said spiral slit; and
    activating a laser coupled to said side firing laser head and configured to produce laser radiation.

18. The method of claim 17, further comprising allowing laser radiation to be emitted laterally.

19. The method of claim 18, wherein said allowing further comprises allowing laser radiation to be emitted through said spiral slit.

20. The method of claim 18, further comprising preventing laser radiation from being emitted longitudinally.

21. The method of claim 20, wherein said allowing further comprises allowing laser radiation to be emitted through said spiral slit in a manner to substantially affect the patient's root canal.

22. The method of claim 21, wherein said preventing further comprises preventing laser radiation from substantially affecting the nerves located at a apical end of the root canal.

23. The method of claim 22, further comprising substantially sterilizing the inner cavity of the root canal.

24. The method of claim 23, further comprising melting the inner dentinal walls of the root canal, such that the tubules are substantially sealed.

25. The method of claim 17, wherein said adjusting said gaps in said spiral slit includes varying the diameter of at least a portion of the laser head.

* * * * *

UNITED STATES PATENT AND TRADEMARK OFFICE
CERTIFICATE OF CORRECTION

PATENT NO. : 7,040,892 B2 Page 1 of 1
APPLICATION NO. : 10/386117
DATED : May 9, 2006
INVENTOR(S) : Hirszowicz, Eran It is certified that error appears in the above-identified patent and that said Letters Patent is hereby corrected as shown below:

On the title page Item (75) should read: Inventors: Eran Hirszowicz, Ramat Gan (IL);
Yemini Raanan, Kfar Vitkin (IL);
Ytzhak Rozenberg, Ramat Gan (IL);
Adam Stabholz, Jerusalem (IL)

Signed and Sealed this

Twenty-second Day of August, 2006

JON W. DUDAS
*Director of the United States Patent and Trademark Office*